(12) United States Patent
Ding et al.

(10) Patent No.: US 6,358,556 B1
(45) Date of Patent: *Mar. 19, 2002

(54) DRUG RELEASE STENT COATING

(75) Inventors: Ni Ding, Plymouth, MN (US); Michael N. Helmus, Long Beach, CA (US)

(73) Assignee: Boston Scientific Corporation, Natick, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/012,443

(22) Filed: Jan. 23, 1998

Related U.S. Application Data (60) Division of application No. 08/663,490, filed on Jun. 13, 1996, now Pat. No. 5,837,313, which is a continuation-in-part of application No. 08/526,273, filed on Sep. 11, 1995, now abandoned, and a continuation-in-part of application No. 08/424,884, filed on Apr. 19, 1995, now abandoned.

(51) Int. Cl.[7] .............................. B05D 3/04; B05D 3/06; A61L 9/18

(52) U.S. Cl. ..................... 427/2.24; 427/2.25; 427/2.28; 427/2.3; 427/2.31; 427/496; 427/535; 427/551

(58) Field of Search ............................ 623/1, 2, 11, 12; 424/422, 423, 424; 427/2.1, 2.24, 2.25, 2.28, 2.3, 2.31, 488, 496, 533, 535, 551

(56) References Cited

U.S. PATENT DOCUMENTS

| 3,932,627 A | 1/1976 | Margraf |
|---|---|---|
| 4,292,965 A | 10/1981 | Nash et al. |
| 4,613,665 A | 9/1986 | Larm |

(List continued on next page.)

FOREIGN PATENT DOCUMENTS

| EP | 0623354 | 11/1994 |
|---|---|---|
| EP | 0 734721 A2 | 10/1996 |
| JP | 03-297469 | 12/1991 |
| JP | 3297469 A * | 12/1991 |
| JP | 06-121828 | 6/1994 |
| JP | 08-33718 | 2/1996 |
| WO | WO 91/12779 | 9/1991 |
| WO | WO 92/15286 | 9/1992 |
| WO | WO 94/21308 | 9/1994 |
| WO | WO 94/21309 | 9/1994 |
| WO | PCT/IB 96/00272 | 6/1996 |

OTHER PUBLICATIONS

Baxter Healthcare Corp. Duraflo Biocompatible Treatment.
Ludwig K. von Segesser, MD., "Heparin–Bonded Surfaces in Extracorporeal Membrane Oxygenation for Cardiac Support", The Society of thoracic Surgeons, (1996).
Li–Chien Hsu, "Principles of Heparin–Coating Techniques", Perfusin 6: 209–219 (1991).
J.M. Toomasian et al., "Evaluation of Duraflo II Heparin Coating in Prolonged Extracorporeal Membrane Oxygenation", ASAIO Trans 34: 410–14 (1988).
S.D. Tong et al., "Non–Thrombogenic Hemofiltration System for Acute Renal Failure Treatment", ASAIO Trans. 38: M702–M706 (1992).

(List continued on next page.)

*Primary Examiner*—Shrive P. Beck
*Assistant Examiner*—Jennifer Kolb Michener (57) ABSTRACT

A method of coating implantable open lattice metallic stent prosthesis is disclosed which includes sequentially applying a plurality of relatively thin outer layers of a coating composition comprising a solvent mixture of uncured polymeric silicone material and crosslinker and finely divided biologically active species, possibly of controlled average particle size, to form a coating on each stent surface. The coatings are cured in situ and the coated, cured prosthesis are sterilized in a step that includes preferred pretreatment with argon gas plasma and exposure to gamma radiation electron beam, ethylene oxide, steam.

21 Claims, 7 Drawing Sheets

U.S. PATENT DOCUMENTS

| | | | |
|---|---|---|---|
| 4,655,771 A | 4/1987 | Wallsten | |
| 4,872,867 A | 10/1989 | Joh et al. | |
| 4,886,062 A | 12/1989 | Wiktor | |
| 4,916,193 A | 4/1990 | Tang et al. | |
| 4,954,126 A | 9/1990 | Wallsten | |
| 4,994,071 A | 2/1991 | McGregor | |
| 5,061,275 A | 10/1991 | Wallsten et al. | |
| 5,064,435 A * | 11/1991 | Porter | 623/12 |
| 5,092,877 A | 3/1992 | Pinchuk | |
| 5,163,952 A | 11/1992 | Froix | |
| 5,180,366 A | 1/1993 | Woods | |
| 5,182,317 A | 1/1993 | Winters et al. | |
| 5,185,408 A | 2/1993 | Tang et al. | |
| 5,226,913 A | 7/1993 | Pinchuk | |
| 5,258,020 A | 11/1993 | Froix | |
| 5,262,451 A | 11/1993 | Winters et al. | |
| 5,292,802 A | 3/1994 | Rhee et al. | |
| 5,304,121 A | 4/1994 | Sahatjian | |
| 5,308,889 A | 5/1994 | Rhee et al. | |
| 5,338,770 A | 8/1994 | Winters et al. | |
| 5,342,348 A | 8/1994 | Kaplan | |
| 5,356,433 A | 10/1994 | Rowland et al. | |
| 5,380,299 A | 1/1995 | Fearnot et al. | |
| 5,415,619 A * | 5/1995 | Lee et al. | 600/36 |
| 5,419,760 A | 5/1995 | Narciso, Jr. | |
| 5,429,618 A | 7/1995 | Keogh | |
| 5,447,724 A | 9/1995 | Helmus et al. | |
| 5,449,382 A | 9/1995 | Dayton | |
| 5,464,650 A | 11/1995 | Berg et al. | |
| 5,486,357 A * | 1/1996 | Narayanan | 424/78.17 |
| 5,545,208 A | 8/1996 | Wolff et al. | |
| 5,578,075 A | 11/1996 | Dayton | |
| 5,605,696 A * | 2/1997 | Eury et al. | 424/423 |
| 5,624,411 A * | 4/1997 | Tuch | 604/265 |
| 5,643,580 A * | 7/1997 | Subramaniam | 424/400 |
| 5,662,712 A * | 9/1997 | Pathak et al. | 623/12 |
| 5,688,855 A * | 11/1997 | Stoy et al. | 524/505 |
| 5,697,967 A * | 12/1997 | Dinh et al. | 623/1 |
| 5,700,559 A * | 12/1997 | Sheu et al. | 428/319.7 |
| 5,716,981 A | 2/1998 | Hunter et al. | |
| 5,735,897 A * | 4/1998 | Buirge | 623/11 |
| 6,096,070 A | 8/2000 | Ragheb et al. | |

OTHER PUBLICATIONS

Bergstrom, Reduction of fibrinogen adsorption on PEG–coated polystyrene surfaces, 1992, p. 779–790, Baxter Healthccare Corp. Duraflo Biocompatible Treatment.

Michael N. Helmus, "Medical Device Design—A Systems Approach: Central Venous Catheters", (1990).

Polysciences Inc., TDMAC–Heparin Coatings, Nov. 1988, Data Sheet #172.

Barbucci, et al., Coating of Commercially available materials with a new heparinizable material, 1991, pp. 1259–1274.

Michael N. Helmus, Grant Application–Ionic–Hydrophilic Density: Platelet/Monocyte Adherence 12/81 12/84, pp. 13, 14, 26–31.

Dennis E. Chenoweth, Complement Activation in Extracorporeal Circuits, pp. 306–329.

Jeffrey A. Hubbell, Ph.D., Jul.–Sep. 1993 Pharmacologic Modification of Materials, 1215–1275.

Glenn P. Gradlee, MD, Heparin–Coated Cardiopulmonary Bypass Circuits, Journal of Cardiothoracic and Vascular Anesthesia, vol. 8, No. 2, Apr. 1994, pp. 213–222.

K. Isihara, H. Hanyuda, and N. Nakabayashi, Synthesis of Phospholipid polymers having a urethane bond . . . , Biomaterials, 1995, pp. 873–879.

J. Sanchez, G. Elgue, J. Riesenfeld and P. Olsson, Control of Contact activiation on end–point immobilized heparin, The role of antithrombin and the specific antithrombin–binding sequence, 1995, pp. 655–661, Journal of Biomedical Materials Research.

Cardiology Conference European Society of Cardiology Conference Clinica, Sep. 4, 1995, pp. 24–26.

Mansoor Amjii and Kinam Park, "Surface Modification of Polymeric Biomaterials with Poly(Ehtylene Oxide), Albumin, and Heparin For Reduced Thrombogenicity", Purdue University, School of Pharmacy, West Lafayette, IN, 47907.

* cited by examiner

DRUG RELEASE STENT COATING

CROSS-REFERENCE TO RELATED APPLICATIONS

The present application is a divisional of application Ser. No. 08/663,490 filed Jun. 13, 1996 now U.S. Pat. No. 5,887,313 which is a Continuation-In-Part of copending application Ser. No. 08/526,273, filed Sep. 11, 1995, and a Continuation-In-Part of copending application Ser. No. 08/424,884, filed Apr. 19, 1995, all portions of the parent applications not contained in this application being deemed incorporated by reference for any purpose. Cross-reference is also made to application Ser. No. 08/663,518, entitled "DRUG RELEASE STENT COATING AND PROCESS", filed of even date and of common inventorship and assignee, that is also a Continuation-In-Part of both above-referenced patent applications. Any portion of that application that is not contained herein is also deemed to be incorporated by reference for any purpose.

BACKGROUND OF THE INVENTION

1. Field of the Invention

The present invention relates generally to therapeutic expandable stent prosthesis for implantation in body lumens, e.g., vascular implantation and, more particularly, to a process for providing biostable elastomeric coatings on such stents which incorporate biologically active species having controlled release characteristics directly in the coating structure.

2. Related Art

In surgical or other related invasive medicinal procedures, the insertion and expansion of stent devices in blood vessels, urinary tracts or other difficult to access places for the purpose of preventing restenosis, providing vessel or lumen wall support or reinforcement and for other therapeutic or restorative functions has become a common form of long-term treatment. Typically, such prosthesis are applied to a location of interest utilizing a vascular catheter, or similar transluminal device, to carry the stent to the location of interest where it is thereafter released to expand or be expanded in situ. These devices are generally designed as permanent implants which may become incorporated in the vascular or other tissue which they contact at implantation.

One type of self-expanding stent has a flexible tubular body formed of several individual flexible thread elements each of which extends in a helix configuration with the centerline of the body serving as a common axis. The elements are wound in a common direction, but are displaced axially relative to each other and meet, under crossing a like number of elements also so axially displaced, but having the opposite direction of winding. This configuration provides a resilient braided tubular structure which assumes stable dimensions upon relaxation. Axial tension produces elongation and corresponding diameter contraction that allows the stent to be mounted on a catheter device and conveyed through the vascular system as a narrow elongated device. Once tension is relaxed in situ, the device at least substantially reverts to its original shape. Prosthesis of the class including a braided flexible tubular body are illustrated and described in U.S. Pat. Nos. 4,655,771 and 4,954,126 to Wallsten and U.S. Pat. No. 5,061,275 to Wallsten et al.

Implanted stents have also been used to carry medicinal agents, such as thrombolytic agents. U.S. Pat. No. 5,163,952 to Froix discloses a thermal memoried expanding plastic stent device which can be formulated to carry a medicinal agent by utilizing the material of the stent itself as an inert polymeric drug carrier. Pinchuk, in U.S. Pat. No. 5,092,877, discloses a stent of a polymeric material which may be employed with a coating associated with the delivery of drugs. Other patents which are directed to devices of the class utilizing bio-degradable or bio-sorbable polymers include Tang et al, U.S. Pat. No. 4,916,193, and MacGregor, U.S. Pat. No. 4,994,071. Sahatjian in U.S. Pat. No. 5,304,121, discloses a coating applied to a stent consisting of a hydrogel polymer and a preselected drug; possible drugs include cell growth inhibitors and heparin. A further method of making a coated intravascular stent carrying a therapeutic material in which a polymer coating is dissolved in a solvent and the therapeutic material dispersed in the solvent and the solvent thereafter evaporated is described in Berg et al, U.S. Pat. No. 5,464,650, issued Nov. 5, 1995 and corresponding to European patent application 0 623 354 A1 published Nov. 9, 1994.

An article by Michael N. Helmus (a co-inventor of the present invention) entitled "Medical Device Design—A Systems Approach: Central Venous Catheters", 22nd International Society for the Advancement of Material and Process Engineering Technical Conference (1990) relates to polymer/drug/membrane systems for releasing heparin. Those polymer/ drug/membrane systems require two distinct layers to function.

The above cross-referenced grandparent application supplies an approach that provides long-term drug release, i.e., over a period of days or even months, incorporated in a controlled-release system. The parent application and present invention provide a process for coating such stents including techniques that enable the initial burst effect of drug elation to be controlled and the drug release kinetic profile associated with long-term therapeutic effect to be modified.

Metal stents of like thickness and weave generally have better mechanical properties than polymeric stents. Metallic vascular stents braided of even relatively fine metal filament can provide a large amount of strength to resist inwardly directed circumferential pressure in blood vessels. In order for a polymer material to provide comparable strength characteristics, a much thicker-walled structure or heavier, denser filament weave is required. This, in turn, reduces the cross-sectional area available for flow through the stent and/or reduces the relative amount of open space available in the structure. In addition, when applicable, it is usually more difficult to load and deliver polymeric stents using vascular catheter delivery systems.

It will be noted, however, that while certain types of stents such as braided metal stents may be superior to others for some applications, the process of the present invention is not limited in that respect and may be used to coat a wide variety of devices. The present invention also applies, for example, to the class of stents that are not self-expanding including those which can be expanded, for instance, with a balloon. Polymeric stents, of all kinds can be coated using the process. Thus, regardless of particular detailed embodiments the use of the invention is not considered or intended to be limited with respect either to stent design or materials of construction. Further, the present invention may be utilized with other types of implant prostheses.

Accordingly, it is a primary object of the present invention to provide a coating process for coating a stent to be used as a deployed stent prosthesis, the coating being capable of long-term delivery of biologically active materials.

Another object of the invention is to provide a process for coating a stent prosthesis using a biostable hydrophobic elastomer in which biologically active species are incorporated within a cured coating.

Still another object of the present invention is to provide a multi-layer coating in which the percentage of active material can vary from layer to layer.

A further object of the present invention is to control or modify aspects of the timed or time variable drug delivery from a stent coating by controlling average particle size in the biologically active species.

Other objects and advantages of the present invention will become apparent to those stilled in the art upon familiarization with the specification and appended claims.

SUMMARY OF THE INVENTION

The present invention provides processes for producing a relatively thin layer of biostable elastomeric material in which an amount of biologically active material is dispersed as a coating on the surfaces of a deployable stent prosthesis. The preferred stent to be coated is a self-expanding, open-ended tubular stent prosthesis. Although other materials, including polymer materials, can be used, in the preferred embodiment, the tubular body is formed of an open braid of fine single or polyfilament metal wire which flexes without collapsing and readily axially deforms to an elongate shape for transluminal insertion via a vascular catheter. The stent resiliently attempts to resume predetermined stable dimensions upon relaxation in situ.

The coating is preferably applied as a mixture, solution or suspension of polymeric material and finely divided biologically active species dispersed in an organic vehicle or a solution or partial solution of such species in a solvent or vehicle for the polymer and/or biologically active species. For the purpose of this application, the term "finely divided" means any type or size of included material from dissolved molecules through suspensions, colloids and particulate mixtures. The active material is dispersed in a carrier material which may be the polymer, a solvent, or both. The coating is preferably applied as a plurality of relatively thin layers sequentially applied in relatively rapid sequence and is preferably applied with the stent in a radially expanded state. In some applications the coating may further be characterized as a composite initial tie coat or undercoat and a composite topcoat. The coating thickness ratio of the topcoat to the undercoat may vary with the desired effect and/or the elution system. Typically these are of different formulations.

The coating may be applied by dipping or spraying using evaporative solvent materials of relatively high vapor pressure to produce the desired viscosity and quickly establish coating layer thicknesses. The preferred process is predicated on reciprocally spray coating a rotating radially expanded stent employing an air brush device. The coating process enables the material to adherently conform to and cover the entire surface of the filaments of the open structure of the stent but in a manner such that the open lattice nature of the structure of the braid or other pattern is preserved in the coated device.

The coating is exposed to room temperature ventilation for a predetermined time (possibly one hour or more) for solvent vehicle evaporation. Thereafter the polymeric precuser material is cured at room temperature or elevated temperatures or the solvent evaporated away from the dissolved polymer as the case may be. Curing is defined as the process of converting the elastomeric or polymeric material into the finished or useful state by the application of heat and/or chemical agents which include physical-chemical charges. Where, for example, polyurethane thermoplastic elastomers are used, solvent evaporation can occur at room temperature rendering the polymeric material useful for controlled drug release without further curing. Non-limiting examples of curing according to this definition include the application of heat and/or chemical agents and the evaporation of solvent which may induce physical and/or chemical changes.

The ventilation time and temperature for cure are determined by the particular polymer involved and particular drugs used. For example, silicone or polysiloxane materials (such as polydimethylsiloxane) have been used successfully. These materials are applied as pre-polymer in the coating composition and must thereafter be cured. The preferred species have a relatively low cure temperatures and are known as a room temperature vulcanizable (RTV) materials. Some polydimethylsiloxane materials can be cured, for example, by exposure to air at about 90° C. for a period of time such as 16 hours. A curing step may be implemented both after application of a certain number of lower undercoat layers and the topcoat layers or a single curing step used after coating is completed.

The coated stents may thereafter be subjected to a post-cure sterilization process which includes an inert gas plasma treatment, and then exposure to gamma radiation, electron beam, ethylene oxide (ETO) or steam sterilization may also be employed.

In the plasma treatment, unconstrained coated stents are placed in a reactor chamber and the system is purged with nitrogen and a vacuum applied to about 20–50 mTorr. Thereafter, inert gas (argon, helium or mixture of them) is admitted to the reaction chamber for the plasma treatment. A highly preferred method of operation consists of using argon gas, operating at a power range from 200 to 400 watts, a flow rate of 150–650 standard ml per minute, which is equivalent to about 100–450 mTorr, and an exposure time from 30 seconds to about 5 minutes. The stents can be removed immediately after the plasma treatment or remain in the argon atmosphere for an additional period of time, typically five minutes.

After the argon plasma pretreatment, the coated and cured stents are subjected to gamma radiation sterilization nominally at 2.5–3.5 Mrad. The stents enjoy full resiliency after radiation whether exposed in a constrained or non-constrained status. It has been found that constrained stents subjected to gamma sterilization without utilizing the argon plasma pretreatment lose resiliency and do not recover at a sufficient or appropriate rate.

The elastomeric material that forms a major constituent of the stent coating should possess certain properties. It is preferably a suitable hydrophobic biostable elastomeric material which does not degrade and which minimizes tissue rejection and tissue inflammation and one which will undergo encapsulation by tissue adjacent to the stent implantation site. Polymers suitable for such coatings include silicones (e.g., polysiloxanes and substituted polysiloxanes), polyurethanes (including polycarbonate urethanes), thermoplastic elastomers in general, ethylene vinyl acetate copolymers, polyolefin elastomers, EPDM ethylene-propylene terpolymer rubbers and polyamide elastomers. The above-referenced materials are considered hydrophobic with respect to the contemplated environment of the invention.

Agents suitable for incorporation include antithrobotics, anticoagulants, antiplatelet agents, thrombolytics, antiproliferatives, antinflammatories, agents that inhibit hyperplasia and in particular restenosis, smooth muscle cell inhibitors, antibiotics growth factors, growth factor inhibitors, cell adhesion inhibitors, cell adhesion promoters and drugs that may enhance the formation of healthy neointimal tissue, including endothelial cell regeneration. The positive action may come from inhibiting particular cells (e.g., smooth muscle cells) or tissue formation (e.g., fibromuscular tissue) while encouraging different cell migration (e.g., endothelium) and tissue formation (neointimal tissue).

The preferred materials for fabricating the braided stent include stainless steel, tantalum, titanium alloys including nitinol (a nickel titanium, thermomemoried alloy material), and certain cobalt alloys including cobalt-chromium-nickel alloys such as ELGILOY® and PHYNOX®. Further details concerning the fabrication and details of other aspects of the stents themselves, may be gleaned from the above referenced U.S. Pat. Nos. 4,655,771 and 4,954,126 to Wallsten and 5,061,275 to Wallsten et al. To the extent additional information contained in the above-referenced patents is necessary for an understanding of the present invention, they are deemed incorporated by reference herein.

Various combinations of polymer coating materials can be coordinated with biologically active species of interest to produce desired effects when coated on stents to be implanted in accordance with the invention. Loadings of therapeutic material may vary. The mechanism of incorporation of the biologically active species into the surface coating, and egress mechanism depend both on the nature of the surface coating polymer and the material to be incorporated. The mechanism of release also depends on the mode of incorporation. The material may elute via interparticle paths or be administered via transport or diffusion through the encapsulating material itself.

For the purposes of this specification, "elution" is defined as any process of release that involves extraction or release by direct contact of the material with bodily fluids through the interparticle paths connected with the exterior of the coating. "Transport" or "diffusion" are defined to include a mechanism of release in which a material released traverses through another material.

The desired release rate profile can be tailored by varying the coating thickness, the radial distribution (layer to layer) of bioactive materials, the mixing method, the amount of bioactive material, the combination of different matrix polymer materials at different layers, and the crosslink density of the polymeric material. The crosslink density is related to the amount of crosslinking which takes place and also the relative tightness of the matrix created by the particular crosslinking agent used. This, during the curing process, determines the amount of crosslinking and so the crosslink density of the polymer material. For bioactive materials released from the crosslinked matrix, such as heparin, a crosslink structure of greater density will increase release time and reduce burst effect.

Additionally, with eluting materials such as heparin, release kinetics, particularly initial drug release rate, can be affected by varying the average dispersed particle size. The observed initial release rate or burst effect may be substantially reduced by using smaller particles, particularly if the particle size is controlled to be less than about 15 microns and the effect is even more significant in the particle size range of $\leq 10$ microns, especially when the coating thickness is not more than about 50 $\mu m$ and drug loading is about 25–45 weight percent.

It will also be appreciated that an unmedicated silicone thin top layer provides an advantage over drug containing top coat. Its surface has a limited porosity and is generally smooth, which may be less thrombogeneous and may reduce the chance to develop calcification, which occurs most often on the porous surface.

BRIEF DESCRIPTION OF THE DRAWINGS

In the drawings, wherein like numerals designate like parts throughout the same.

DETAILED DESCRIPTION

According to the present invention, the stent coatings incorporating biologically active materials for timed delivery in situ in a body lumen of interest are preferably sprayed in many thin layers from prepared coating solutions or suspensions. The steps of the process are illustrated generally in FIG. 1. The coating solutions or suspensions are prepared at 10 as will be described later. The desired amount of crosslinking agent is added to the suspension/solution as at 12 and material is then agitated or stirred to produce a homogenous coating composition at 14 which is thereafter transferred to an application container or device which may be a container for spray painting at 16. Typical exemplary preparations of coating solutions that were used for heparin and dexamethasone appear next.

General Preparation of Heparin Coating Composition

Silicone was obtained as a polymer precursor in solvent (xylene) mixture. For example, a 35% solid silicone weight content in xylene was procured from Applied Silicone, Part #40,000. First, the silicone-xylene mixture was weighed. The solid silicone content was determined according to the vendor's analysis. Precalculated amounts of finely divided heparin (2–6 microns) were added into the silicone, then tetrahydrofuron (THF) HPCL grade (Aldrich or EM) was added. For a 37.5% heparin coating, for example: $W_{silicone}=5$ g; solid percent=35%; $W_{hep}=5\times0.35\times0.375/(0.625)=1.05$ g. The amount of THF needed (44 ml) in the coating solution was calculated by using the equation $W_{silicone\ solid}/V_{THF}=0.04$ for a 37.5% heparin coating solution). Finally, the manufacturer crosslinker solution was added by using Pasteur P-pipet. The amount of crosslinker added was formed to effect the release rate profile. Typically, five drops of crosslinker solution were added for each five grams of silicone-xylene mixture. The crosslinker may be any suitable and compatible agent including platinum and peroxide based materials. The solution was stirred by using the stirring rod until the suspension was homogenous and milk-like. The coating solution was then transferred into a paint jar in condition for application by air brush.

General Preparation of Dexamethasone Coating Composition

Silicone (35% solution as above) was weighed into a beaker on a Metler balance. The weight of dexamethasone free alcohol or acetate form was calculated by silicone weight multiplied by 0.35 and the desired percentage of dexamethasone (1 to 40%) and the required amount was then weighed. Example: $W_{silicone}=5$ g; for a 10% dexamethasone coating, $W_{dex}=5\times0.35\times0.1/0.9=0.194$ g and THF needed in the coating solution calculated. $W_{silicone\ solid}/V_{THF}=0.06$ for a 10% dexamethasone coating solution. Example: $W_{silicone}=5$ g; $V_{THF}=5\times0.35/0.06\approx29$ ml. The dexamethasone was weighed in a beaker on an analytical balance and half the total amount of THF was added. The solution was stirred well to ensure full dissolution of the dexamethasone. The stirred DEX-THF solution was then transferred to the silicone container. The beaker was washed with the remaining THF and this was transferred to the silicone container. The crosslinker was added by using a Pasteur pipet. Typically, five drops of crosslinker were used for five grams of silicone.

The application of the coating material to the stent was quite similar for all of the materials and the same for the heparin and dexamethasone suspensions prepared as in the above Examples. The suspension to be applied was transferred to an application device, typically a paint jar attached to an air brush, such as a Badger Model 150, supplied with a source of pressurized air through a regulator (Norgren, 0–160 psi). Once the brush hose was attached to the source of compressed air downstream of the regulator, the air was applied. The pressure was adjusted to approximately 15–25 psi and the nozzle condition checked by depressing the trigger.

Any appropriate method can be used to secure the stent for spraying and rotating fixtures were utilized successfully in the laboratory. Both ends of the relaxed stent were fastened to the fixture by two resilient retainers, commonly alligator clips, with the distance between the clips adjusted so that the stent remained in a relaxed, unstretched condition. The rotor was then energized and the spin speed adjusted to the desired coating speed, nominally about 40 rpm.

With the stent rotating in a substantially horizontal plane, the spray nozzle was adjusted so that the distance from the nozzle to the stent was about 2–4 inches and the composition was sprayed substantially horizontally with the brush being directed along the stent from the distal end of the stent to the proximal end and then from the proximal end to the distal end in a sweeping motion at a speed such that one spray cycle occurred in about three stent rotations. Typically a pause of less than one minute, normally about one-half minute, elapsed between layers. Of course, the number of coating layers did and will vary with the particular application. For example, for a coating level of 3–4 mg of heparin per $cm^2$ of projected area, 20 cycles of coating application are required and about 30 ml of solution will be consumed for a 3.5 mm diameter by 14.5 cm long stent.

The rotation speed of the motor, of course, can be adjusted as can the viscosity of the composition and the flow rate of the spray nozzle as desired to modify the layered structure. Generally, with the above mixes, the best results have been obtained at rotational speeds in the range of 30–50 rpm and with a spray nozzle flow rate in the range of 4–10 ml of coating composition per minute, depending on the stent size. It is contemplated that a more sophisticated, computer-controlled coating apparatus will successfully automate the process demonstrated as feasible in the laboratory.

Figure 1:
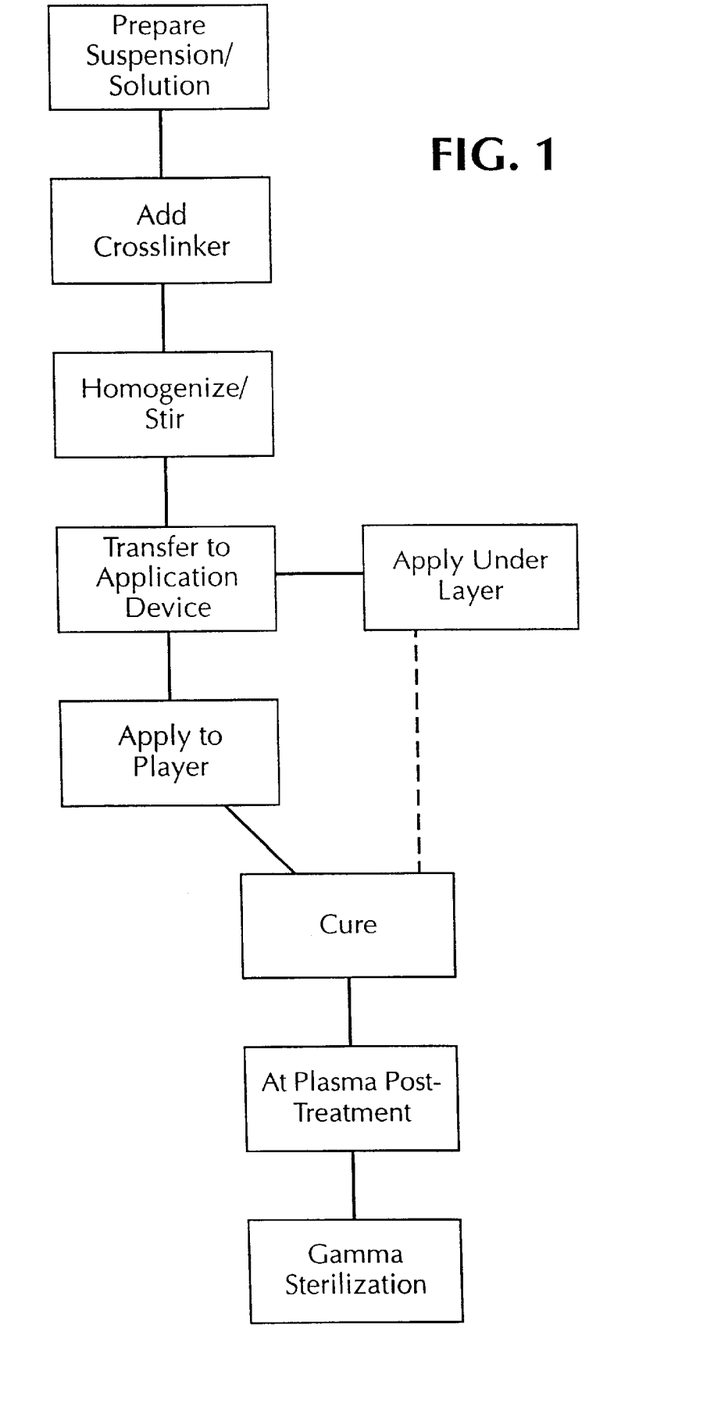
FIG. 1 is a schematic flow diagram illustrating the steps of the process of the invention.
Figure 2:
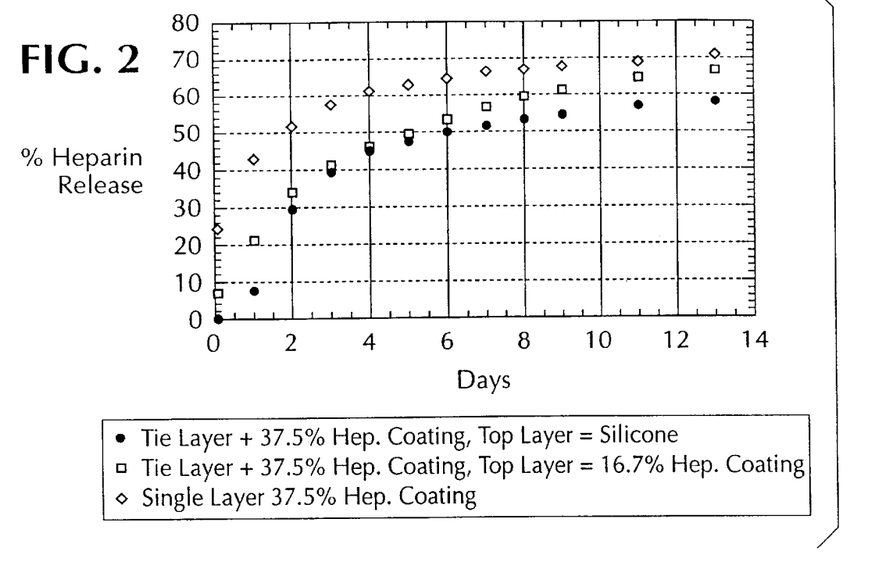
FIG. 2 represents a release profile for a multi-layer system showing the percentage of heparin released over a two-week period.
Figure 3:
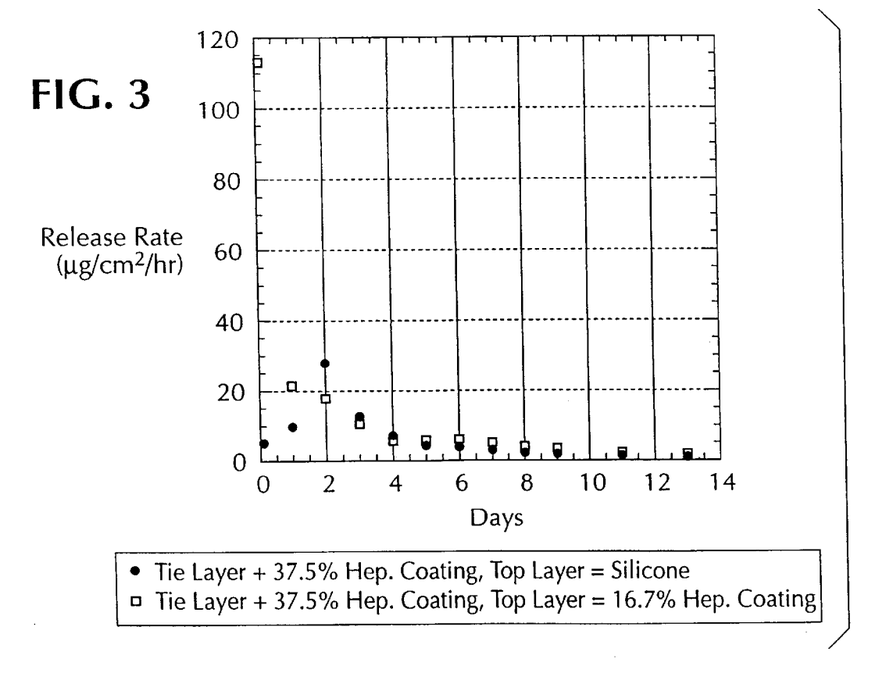
FIG. 3 represents a release profile for a multi-layer system showing the relative release rate of heparin over a two-week period.

Several applied layers make up what is called the tie layer as at 18 and thereafter additional upper layers, which may be of a different composition with respect to bioactive material, the matrix polymeric materials and crosslinking agent, for example, are applied as the top layer as at 20. The application of the top layer follows the same coating procedure as the tie layer with the number and thickness of layers being optional. Of course, the thickness of any layer can be adjusted by modifying the speed of rotation of the stent and the spraying conditions. Generally, the total coating thickness is controlled by the number of spraying cycles or thin coats which make up the total coat.

As shown at 22 in FIG. 1, the coated stent is thereafter subjected to a curing step in which the pre-polymer and crosslinking agents cooperate to produce a cured polymer matrix containing the biologically active species. The curing process involves evaporation of the solvent xylene, THF, etc. and the curing and crosslinking of the polymer. Certain silicone materials can be cured at relatively low temperatures, (i.e. RT-50° C.) in what is known as a room temperature vulcanization (RTV) process. More typically, however, the curing process involves higher temperature curing materials and the coated stents are put into an oven at approximately 90° C. or higher for approximately 16 hours. The temperature may be raised to as high as 150° C. for dexamethasone containing coated stents. Of course, the time and temperature may vary with particular silicones, crosslinkers, and biologically active species.

Stents coated and cured in the manner described need to be sterilized prior to packaging for future implantation. For sterilization, gamma radiation is a preferred method particularly for heparin containing coatings; however, it has been found that stents coated and cured according to the process of the invention subjected to gamma sterilization may be too slow to recover their original posture when delivered to a vascular or other lumen site using a catheter unless a pretreatment step as at 24 is first applied to the coated, cured stent.

The pretreatment step involves an argon plasma treatment of the coated, cured stents in the unconstrained configuration. In accordance with this procedure, the stents are placed in a chamber of a plasma surface treatment system such as a Plasma Science 350 (Himont/Plasma Science, Foster City, Calif.). The system is equipped with a reactor chamber and RF solid-state generator operating at 13.56 mHz and from 0–500 watts power output and being equipped with a microprocessor controlled system and a complete vacuum pump package. The reaction chamber contains an unimpeded work volume of 16.75 inches (42.55 cm) by 13.5 inches (34.3 cm) by 17.5 inches (44.45 cm) in depth.

In the plasma process, unconstrained coated stents are placed in a reactor chamber and the system is purged with nitrogen and a vacuum applied to 20–50 mTorr. Thereafter, inert gas (argon, helium or mixture of them) is admitted to the reaction chamber for the plasma treatment. A highly preferred method of operation consists of using argon gas, operating at a power range from 200 to 400 watts, a flow rate of 150–650 standard ml per minute, which is equivalent to 100–450 mTorr, and an exposure time from 30 seconds to about 5 minutes. The stents can be removed immediately after the plasma treatment or remain in the argon atmosphere for an additional period of time, typically five minutes.

After this, as shown at 26, the stents are exposed to gamma sterilization at 2.5–3.5 Mrad. The radiation may be carried out with the stent in either the radially non-constrained status—or in the radially constrained status.

With respect to the anticoagulant material heparin, the percentage in the tie layer is nominally from about 20–50% and that of the top layer from about 0–30% active material. The coating thickness ratio of the top layer to the tie layer varies from about 1:10 to 1:2 and is preferably in the range of from about 1:6 to 1:3.

Suppressing the burst effect also enables a reduction in the drug loading or in other words, allows a reduction in the coating thickness, since the physician will give a bolus injection of antiplatelet/anticoagulation drugs to the patient during the stenting process. As a result, the drug imbedded in the stent can be fully used without waste. Tailoring the first day release, but maximizing second day and third day release at the thinnest possible coating configuration will reduce the acute or subcute thrombosis.

Figure 4:
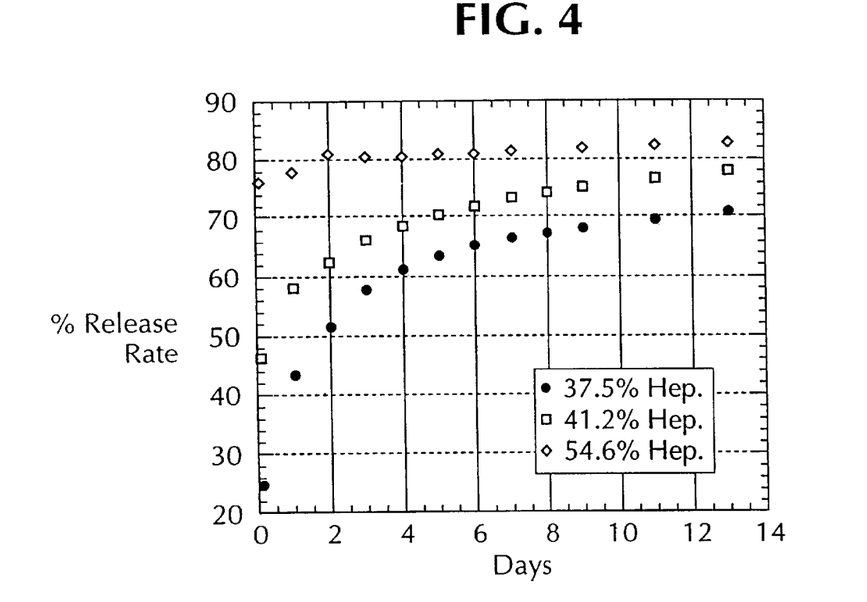
FIG. 4 illustrates a profile of release kinetics for different drug loadings at similar coating thicknesses illustrating the release of heparin over a two-week period.
Figure 5:
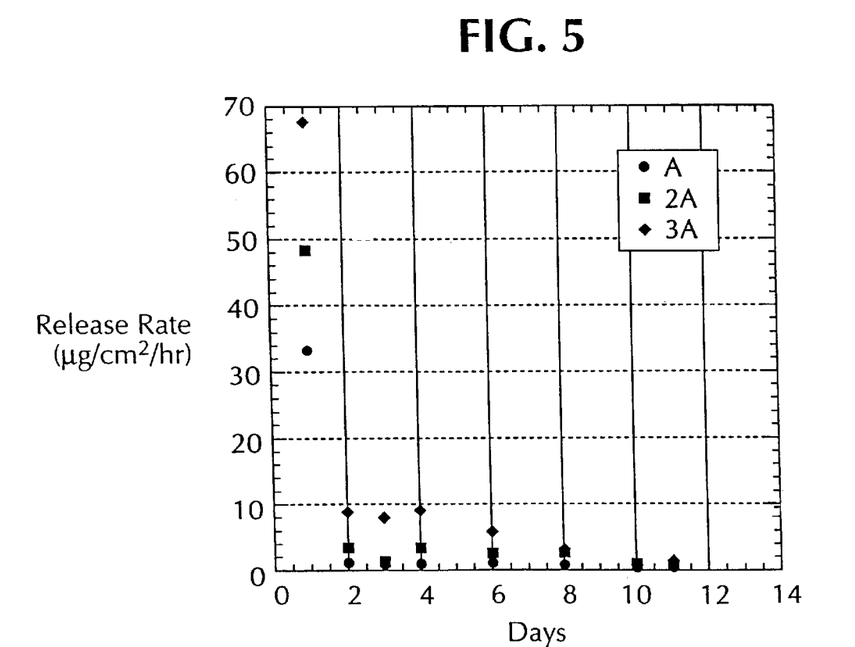
FIG. 5 illustrates drug elution kinetics at a given loading of heparin over a two-week period at different coating thicknesses.
Figure 6:
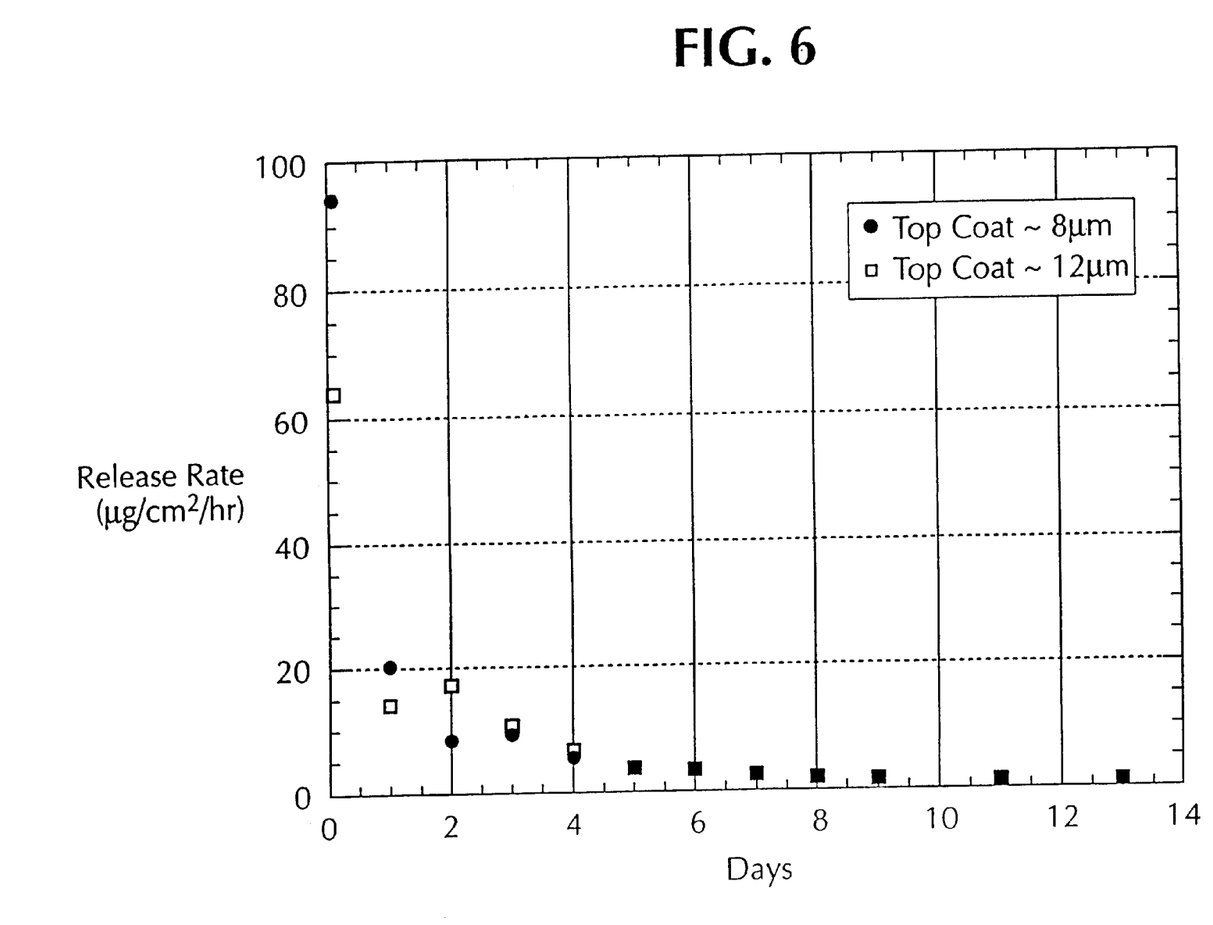
FIG. 6 illustrates the release kinetics in a coating having a given tie-layer thickness for different top coat thicknesses in which the percentage heparin in the tie coat and top coats are kept constant.

FIG. 4 depicts the general effect of drug loading for coatings of similar thickness. The initial elution rate increases with the drug loading as shown in FIG. 5. The release rate also increases with the thickness of the coating at the same loading but tends to be inversely proportional to the thickness of the top layer as shown by the same drug loading and similar tie-coat thickness in FIG. 6.

Figure 7:
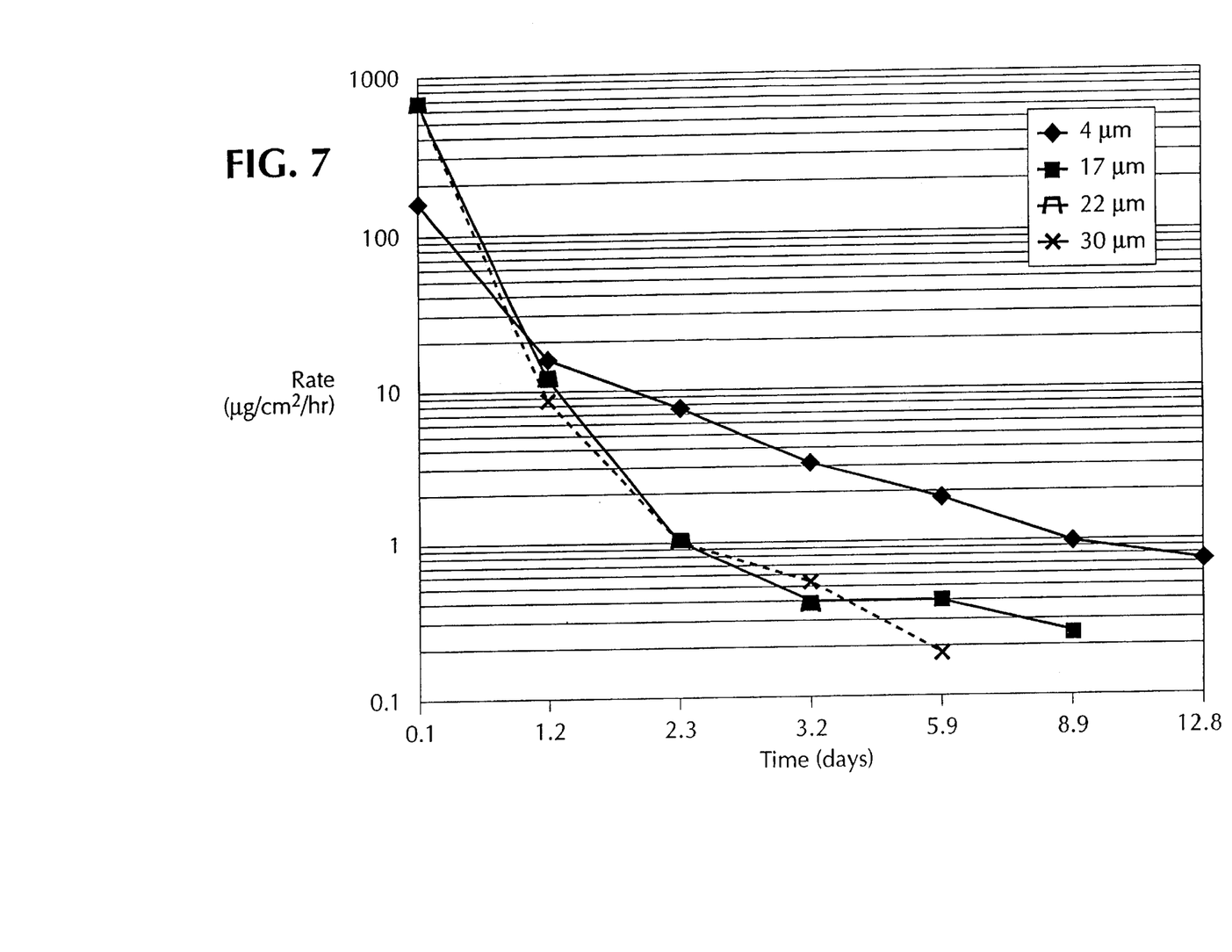
FIG. 7 illustrates the release kinetics of several coatings having an average coating thickness of 25 microns and a heparin loading of 37.5% but using four different average particle sizes.
Figure 8:
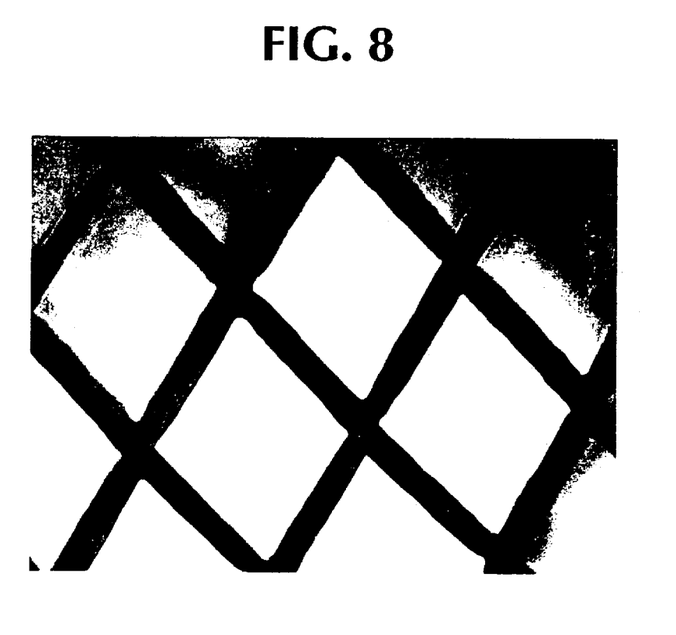
FIGS. 8–11 are photomicrographs of coated stent fragments for the coatings of FIG. 7 having a corresponding average particle size of 4 microns, 17 microns, 22 microns and 30 microns, respectively.
Figure 9:
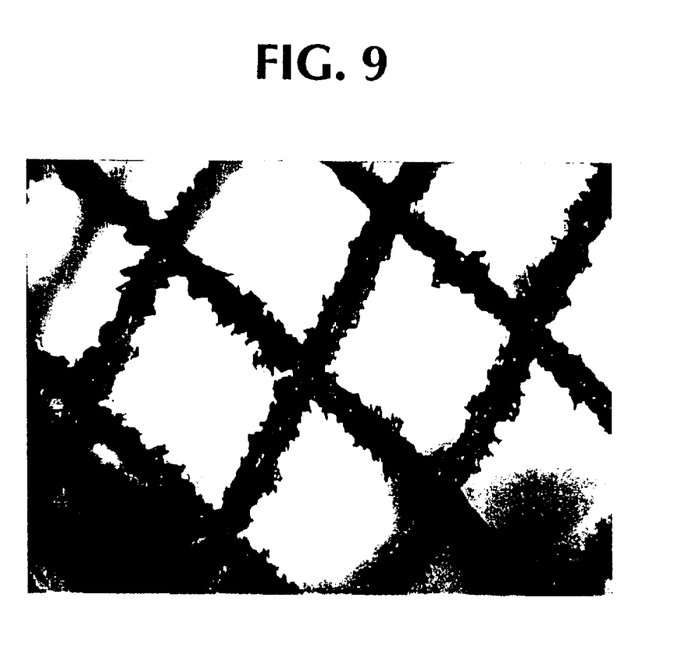
Figure 10:
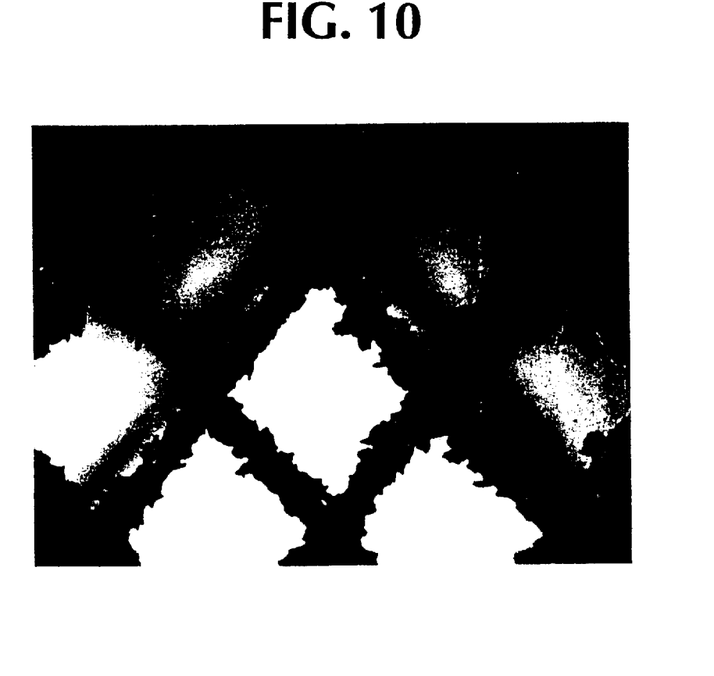
Figure 11:
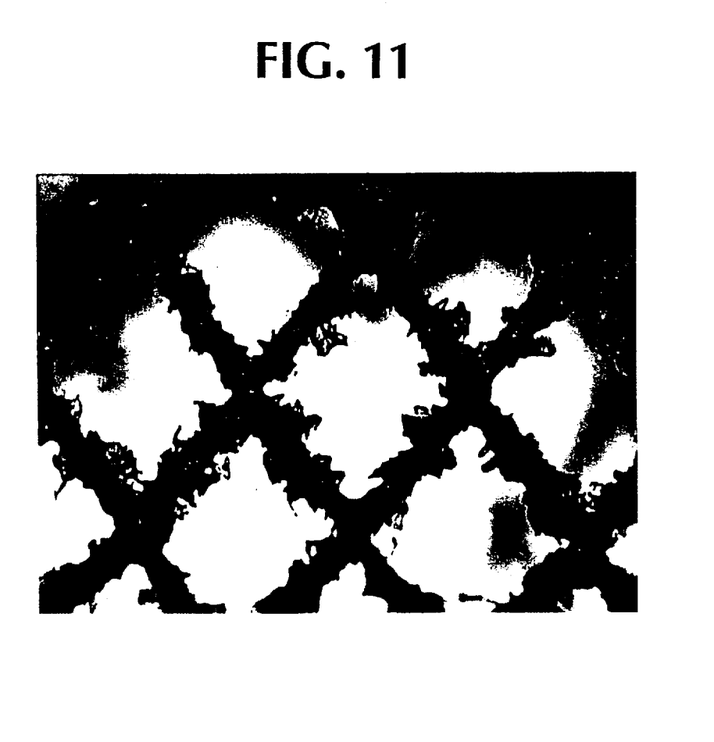

The effect of average particle size is depicted in the FIGS. 7–11 in which coating layers with an average coating thickness of about 25 microns ($\mu$m), prepared and sterilized as above, were provided with dispersed heparin particles (to 37.5% heparin) of several different average particle sizes. FIG. 7 shows plots of elution kinetics for four different sizes of embedded heparin particles. The release took place in phosphate buffer (pH 7.4) at 37° C. The release rate using smaller, particularly 4–6 $\mu$m average sized particles noticeably reduces the initial rate or burst effect and thereafter the elution rate decreases more slowly with time. Average particle sizes above about 15 $\mu$m result in initial release rates approaching bolus elution. This, of course, is less desirable, both from the standpoint of being an unnecessary initial excess and for prematurely depleting the coating of deserved drug material.

In addition, as shown in the photomicrographs of FIGS. 8–11, as the average particle size increases, the morphology of the coating surface also changes. Coatings containing larger particles (FIGS. 9–11) have very rough and irregular surface characteristics. These surface irregularities may be more thrombogenic or exhibit an increased tendency to cause embolization when the corresponding stent is implanted in a blood vessel.

Accordingly, it has been found that the average particle size should generally be controlled below about 15 $\mu$m to reduce the burst effect and preferably should be $\leq$ about 10 $\mu$m for best results. The 4–6 $\mu$m size worked quite successfully in the laboratory. However, it should be noted that larger particle size can also be advantageously used, for instance, when the drug load is low, such as below 25 weight percent. Elution kinetics can be adjusted by a combination of changing the particle size and changing the load or concentration of the dispersed drug material.

What is apparent from the data gathered to date, however, is that the process of the present invention enables the drug elution kinetics to be modified to meet the needs of the particular stent application. In a similar manner, stent coatings can be prepared using a combination of two or more drugs and the drug release sequence and rate controlled. For example, antiproliferation drugs may be combined in the undercoat and anti-thrombotic drugs in the topcoat layer. In this manner, the anti-thrombotic drugs, for example, heparin, will elute first followed by antiproliferation drugs, e.g. dexamethasone, to better enable safe encapsulation of the implanted stent.

The heparin concentration measurement were made utilizing a standard curve prepared by complexing azure A dye with dilute solutions of heparin. Sixteen standards were used to compile the standard curve in a well-known manner.

For the elution test, the stents were immersed in a phosphate buffer solution at pH 7.4 in an incubator at approximately 37° C. Periodic samplings of the solution were processed to determine the amount of heparin eluted. After each sampling, each stent was placed in heparin-free buffer solution.

As stated above, while the allowable loading of the elastomeric material with heparin may vary, in the case of silicone materials heparin may exceed 60% of the total weight of the layer. However, the loading generally most advantageously used is in the range from about 10% to 45% of the total weight of the layer. In the case of dexamethasone, the loading may be as high as 50% or more of the total weight of the layer but is preferably in the range of about 0.4% to 45%.

It will be appreciated that the mechanism of incorporation of the biologically active species into a thin surface coating structure applicable to a metal stent is an important aspect of the present invention. The need for relatively thick-walled polymer elution stents or any membrane overlayers associated with many prior drug elution devices is obviated, as is the need for utilizing biodegradable or reabsorbable vehicles for carrying the biologically active species. The technique clearly enables long-term delivery and minimizes interference with the independent mechanical or therapeutic benefits of the stent itself.

Coating materials are designed with a particular coating technique, coating/drug combination and drug infusion mechanism in mind. Consideration of the particular form and mechanism of release of the biologically active species in the coating allow the technique to produce superior results. In this manner, delivery of the biologically active species from the coating structure can be tailored to accommodate a variety of applications.

Whereas the above examples depict-coatings having two different drug loadings or percentages of biologically active material to be released, this is by no means limiting with respect to the invention and it is contemplated that any number of layers and combinations of loadings can be employed to achieve a desired release profile. For example, gradual grading and change in the loading of the layers can be utilized in which, for example, higher loadings are used in the inner layers. Also layers can be used which have no drug loadings at all. For example, a pulsatile heparin release system may be achieved by a coating in which alternate layers containing heparin are sandwiched between unloaded layers of silicone or other materials for a portion of the coating. In other words, the invention allows untold numbers of combinations which result in a great deal of flexibility with respect to controlling the release of biologically active materials with regard to an implanted stent. Each applied layer is typically from approximately 0.5 microns to 15 microns in thickness. The total number of sprayed layers, of course, can vary widely, from less than 10 to more than 50 layers; commonly, 20 to 40 layers are included. The total thickness of the coating can also vary widely, but can generally be from about 10 to 200 microns.

Whereas the polymer of the coating may be any compatible biostable elastomeric material capable of being adhered to the stent material as a thin layer, hydrophobic materials are preferred because it has been found that the release of the biologically active species can generally be more predictably controlled with such materials. Preferred materials include silicone rubber elastomers and biostable polyurethanes specifically.

This invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

We claim:

1. A process for making an implantable medical prosthesis in which at least a portion of the prosthesis is covered with a coating, wherein the process comprises:
   (a) applying a composition, comprising a polymeric material incorporating a biologically active material, to the portion of the prosthesis to form a coating thereon;
   (b) curing the coating;
   (c) exposing the portion of the prosthesis to an inert gas plasma treatment after the coating is cured; and
   (d) sterilizing the portion of the prosthesis with gamma radiation.

2. The process of claim 1 wherein the inert gas is selected from the group consisting of argon, helium or mixtures thereof.

3. The process of claim 2 wherein the inert gas is argon.

4. The process of claim 1 wherein the portion of the prosthesis is exposed to the inert gas plasma treatment for about 30 seconds to about 5 minutes.

5. The process of claim 4 wherein the portion of the prosthesis is exposed to the inert gas for an additional period of time.

6. The process of claim 5 wherein the additional period of time is about 5 minutes.

7. The process of claim 1 wherein the gamma radiation is about 2.5 to about 3.5 Mrad.

8. The process of claim 1 wherein the coating is cured by a method selected from the group consisting of applying a heat source to the coating and applying a chemical agent to the coating.

9. The process of claim 1 wherein the biologically active material has an average particle size of equal to or less than about 15 $\mu$m.

10. The process of claim 9 wherein the biologically active material has an average particle size of equal to or less than about 10 $\mu$m.

11. The process of claim 9 wherein the coating reduces an initial burst release of the biologically active material upon implantation of the prosthesis as compared to a coating comprising the same biologically active material having an average particle size greater than about 15 $\mu$m.

12. The process of claim 1 wherein the composition comprises about 25–45 weight percent of the biologically active material.

13. The process of claim 1 wherein the biologically active material includes heparin.

14. The process of claim 1 wherein the polymeric material is a hydrophobic elastomeric material.

15. The process of claim 14 wherein the hydrophobic elastomeric material is selected from the group consisting of silicones, polyurethanes, polyamide elastomers, ethylene vinyl acetate copolymers, polyolefin elastomers, ethylene-propylene terpolymer rubbers and combinations thereof.

16. The process of claim 14 wherein the prosthesis is an expandable stent having a tubular metal body having open ends and a sidewall structure having openings therein and wherein the composition is applied to the stent in a manner such that the composition adheringly conforms to the sidewall structure to preserve the openings therein when the stent is expanded.

17. An implantable medical prosthesis prepared according to the process of claim 1.

18. The process of claim 1 Wherein the prosthesis is an expandable stent.

19. The process of claim 18 wherein the expandable stent is self-expanding.

20. A process for making an expandable stent in which at least a portion of the stent is covered with a coating, wherein the process comprises:
   (a) applying a composition, comprising a hydrophobic elastomeric material incorporating a biologically active material, to the portion of the stent to form a coating thereon;
   (b) curing the coating;
   (c) exposing the portion of the stent to an argon plasma treatment after the coating is cured; and
   (d) sterilizing the portion of the stent with gamma radiation.

21. A process for making an expandable stent in which at least a portion of the stent is covered with a coating, wherein the process comprises:
   (a) applying a composition, comprising a polymeric material incorporating a biologically active material, to the portion of the stent to form a coating thereon;
   (b) curing the coating;
   (c) exposing the portion of the stent to an argon plasma treatment for about 30 seconds to about 5 minutes after the coating is cured; and
   (d) sterilizing the portion of the stent with gamma radiation of about 2.5 to about 3.4 Mrad.

* * * * *

UNITED STATES PATENT AND TRADEMARK OFFICE
CERTIFICATE OF CORRECTION

PATENT NO. : 6,358,556 B1
DATED : March 19, 2002
INVENTOR(S) : Ding et al.

It is certified that error appears in the above-identified patent and that said Letters Patent is hereby corrected as shown below:

Title page,
Item [73], Assignee, should read:
-- [73] Assignee: Schneider (USA) Inc. --

Signed and Sealed this

Eighth Day of March, 2005

JON W. DUDAS
*Director of the United States Patent and Trademark Office*